(12) United States Patent
De Nanteuil et al.

(10) Patent No.: US 6,686,358 B2
(45) Date of Patent: *Feb. 3, 2004

(54) BICYCLIC AMINO-PYRAZINONE COMPOUNDS

(75) Inventors: Guillaume De Nanteuil, Suresnes (FR); Philippe Gloanec, Bougival (FR); Tony Verbeuren, Vernouillet (FR); Alain Rupin, Savonnieres (FR); Marie-Odile Vallez, Champs Sur Marne (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 14 days.

This patent is subject to a terminal disclaimer.

(21) Appl. No.: 10/020,433

(22) Filed: Dec. 14, 2001

(65) Prior Publication Data

US 2002/0111341 A1 Aug. 15, 2002

(30) Foreign Application Priority Data

Dec. 14, 2000 (FR) .................................................. 16321

(51) Int. Cl.⁷ .................... A61K 31/33; A61K 31/4985; C07D 471/00; C07D 209/52; C07D 487/02

(52) U.S. Cl. ........................ 514/249; 514/183; 514/357; 514/358; 514/413; 514/423; 544/349; 544/350; 546/112; 546/113; 546/121; 546/290; 546/304; 548/416; 548/452; 548/453; 548/465; 548/570

(58) Field of Search ................................. 514/249, 357, 514/358, 413, 423, 183; 544/349, 350; 546/112, 113, 121, 290, 304; 548/416, 452, 453, 465, 570

(56) References Cited

U.S. PATENT DOCUMENTS 6,277,851 B1 * 8/2001 De Nanteuil et al. ........ 514/249

FOREIGN PATENT DOCUMENTS

WO 9308188 * 4/1993

* cited by examiner

Primary Examiner—Mukund J. Shah
Assistant Examiner—Sudhaker B. Patel
(74) Attorney, Agent, or Firm—The Firm of Hueschen and Sage

(57) ABSTRACT

A compound of formula (I):

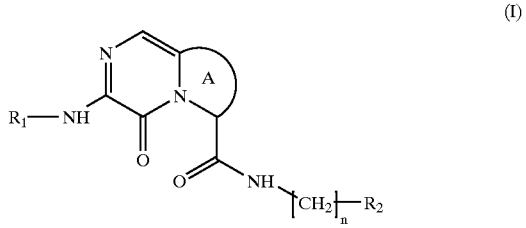

wherein:

$R_1$ represents hydrogen, or linear or branched ($C_1$–$C_6$) alkyl optionally substituted by one or more identical or different groups selected from aryl, heteroaryl, cycloalkyl and heterocycloalkyl,

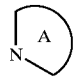

represents a saturated ring having from 4 to 7 ring members that may contain, in addition to nitrogen, one or two hetero atoms selected from O, S and —$NR_3$ groups, wherein $R_3$ represents hydrogen or linear or branched ($C_1$–$C_6$)alkyl, n represents an integer such that $1 \leq n \leq 6$, $R_2$ represents any one of the groups described in the description, their isomers and addition salts thereof with a pharmaceutically acceptable acid or base and medicinal products containing the same are useful as inhibitor of trypsin-related serine proteases and thrombin.

22 Claims, No Drawings

BICYCLIC AMINO-PYRAZINONE COMPOUNDS

BACKGROUND OF THE INVENTION

The present invention relates to new bicyclic amino-pyrazinone compounds, to pharmaceutical compositions containing them and to their use as inhibitors of trypsin-related serine proteases.

One of those serine proteases, thrombin, is the key enzyme for coagulation and plays a central role in venous and arterial thrombosis pathology in view, in particular, of its marked ability to cause autoamplification of the coagulation cascade (F. Toti et al., Sang, Thrombose, Vaisseaux 1992, 4, 483–494 and T. M. Reilly et al., Blood Coagulation and Fibrinolysis 1992, 3, 513–517).

The specific and direct inhibition of thrombin is more efficient and presents fewer risks of haemorrhage than treatment with heparin. Direct inhibitors of thrombin do currently exist, but the drawback of such peptide substances is that they are not active when administered by the oral route.

DESCRIPTION OF THE PRIOR ART

Peptidomimetic compounds having an oral antithrombotic activity have previously been described in the literature. These include, in particular, the boronic acid compounds described in the patent specifications EP 293 881, EP 471 651, EP 615 978 and EP 792 883 and the compounds described in the patent specifications WO 94 29336 and WO 95 23609.

The synthesis of new serine protease inhibitors for the purpose of increasing the potency and selectivity of the compounds previously described in the literature has therefore been of particular interest.

The activity of the new compounds is demonstrated by the increase of various coagulation times.

Furthermore, the compounds are active when administered by the oral route.

DETAILED DESCRIPTION OF THE INVENTION

The present invention relates more specifically to the compounds of formula (I):

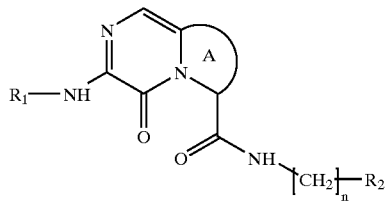

(I)

wherein:

$R_1$ represents a hydrogen atom, or a linear or branched ($C_1$–$C_6$)alkyl group optionally substituted by one or more identical or different groups selected from aryl, heteroaryl, cycloalkyl and heterocycloalkyl,

represents a saturated ring having from 4 to 7 ring members that may contain, in addition to the nitrogen atom, one or two hetero atoms selected from O, S and —$NR_3$ groups, wherein $R_3$ represents a hydrogen atom or a linear or branched ($C_1$–$C_6$)alkyl group, n represents an integer such that $1 \leq n \leq 6$, $R_2$ represents any one of the following groups:

a:

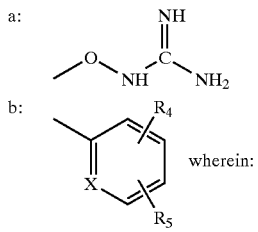

b:

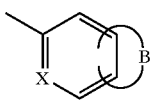 wherein:

X represents a CH group or a nitrogen atom,
$R_4$ represents a hydrogen or halogen atom,
$R_5$ represents any one of the groups:
 $R_a$NHCOHN— wherein $R_a$ represents a hydrogen atom or a linear or branched ($C_1$–$C_6$)alkyl group,
 $R_b$SO$_2$NHCO(NH)$_p$—, wherein $R_b$ represents a linear or branched ($C_1$–$C_6$)-alkyl group and p represents 0 or 1,
 HON=C(NH$_2$)—, HN=C(NHOH)—,
 $R_c$—(CH$_2$)$_m$—Y— wherein:
  Y represents CH$_2$, O, S or $R_a$N,
  m represents a integer such that $0 \leq m \leq 3$,
  $R_c$ represents a saturated or unsaturated heterocycle having 5 or 7 ring members containing from 1 to 4 hetero atoms selected from oxygen, nitrogen and sulphur, the said heterocycle optionally containing one or more carbonyl functions and optionally being substituted by one or more identical or different substituents selected from halogen atoms, linear or branched ($C_1$–$C_6$)alkyl groups, linear or branched ($C_1$–$C_6$)alkoxy groups, and amino groups (optionally substituted by one or two linear or branched ($C_1$–$C_6$)alkyl groups), or c:
 a bicyclic system of formula

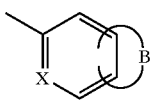

wherein:
 X is as defined hereinbefore and B, together with the carbon atoms to which it is attached, forms an aryl or a saturated or unsaturated heterocycle having 5 or 7 ring members containing from 1 to 4 hetero atoms selected from oxygen, nitrogen and sulphur, the said heterocycle optionally containing at least one carbonyl function and optionally being substituted by one or more identical or different substituents selected from halogen atoms, linear or branched ($C_1$–$C_6$)alkyl groups, linear or branched ($C_1$–$C_6$)alkoxy groups, and amino groups (optionally substituted by one or two linear or branched ($C_1$–$C_6$)alkyl groups), to their isomers, to their N-oxides and to pharmaceutically acceptable addition salts thereof with an acid or a base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid, etc.

Among the pharmaceutically acceptable bases there may be mentioned, without implying any limitation, sodium hydroxide, potassium hydroxide, triethylamine, tert-butylamine, etc.

An aryl group is to be understood as meaning phenyl, biphenylyl or naphthyl, each of those groups optionally being substituted by one or more identical or different groups selected from halogen, linear or branched ($C_1$–$C_6$) alkyl (optionally substituted by a hydroxy group, a carboxy group, an amino group (itself optionally substituted by one or two linear or branched ($C_1$–$C_6$)alkyl groups) or a carbamoyl group (itself optionally substituted by one or two linear or branched ($C_1$–$C_6$)alkyl groups)), linear or branched ($C_1$–$C_6$)alkoxy, hydroxy, linear or branched ($C_1$–$C_6$) trihaloalkyl, linear or branched ($C_1$–$C_6$)trihaloalkoxy, amino (optionally substituted by one or two linear or branched ($C_1$–$C_6$)alkyl groups), linear or branched ($C_1$–$C_6$) alkylcarbonyloxy, carboxymethoxy and carbamoylmethoxy (optionally N-substituted by one or two linear or branched ($C_1$–$C_6$)alkyl groups).

A heteroaryl group is to be understood as meaning an aromatic mono- or bi-cyclic group having from 5 to 12 ring members containing one, two or three hetero atoms selected from oxygen, nitrogen and sulphur, wherein the heteroaryl may optionally be substituted by one or more identical or different groups selected from halogen, linear or branched ($C_1$–$C_6$)alkyl (optionally substituted by a hydroxy group, a carboxy group, an amino group (itself optionally substituted by one or two linear or branched ($C_1$–$C_6$)alkyl groups) or a carbamoyl group (itself optionally substituted by one or two linear or branched ($C_1$–$C_6$)alkyl groups)), hydroxy, linear or branched ($C_1$–$C_6$)alkoxy, linear or branched ($C_1$–$C_6$) trihaloalkyl, phenyl, amino (optionally N-substituted by one or more linear or branched ($C_1$–$C_6$)alkyl groups), carboxymethoxy and carbamoylmethoxy (optionally substituted by one or two linear or branched ($C_1$–$C_6$)alkyl groups). Of the heteroaryl groups, the following may be mentioned without implying any limitation: thienyl, pyridyl, furyl, pyrrolyl, imidazolyl, oxazolyl, isoxazolyl, thiazolyl, isothiazolyl, pyrimidinyl, pyrazinyl, pyridazinyl.

A cycloalkyl group is to be understood as meaning a saturated or unsaturated, mono- or bi-cyclic hydrocarbon group having from 3 to 12 ring members, wherein the ring may optionally be substituted by one or more identical or different groups selected from halogen, linear or branched ($C_1$–$C_6$)alkyl, linear or branched ($C_1$–$C_6$)alkoxy, hydroxy, linear or branched ($C_1$–$C_6$)trihaloalkyl, amino (optionally substituted by one or more linear or branched ($C_1$–$C_6$)alkyl groups) and aryl.

Of the cycloalkyl groups, the following may be mentioned without implying any limitation: cyclopentyl, cyclohexyl, indanyl, tetrahydronaphthyl.

A heterocycloalkyl group is to be understood as meaning a saturated or unsaturated, mono- or bi-cyclic group having from 4 to 12 ring members containing one, two or three hetero atoms selected from oxygen, nitrogen and sulphur, wherein the heterocycle may optionally be substituted by one or more identical or different groups selected from halogen, linear or branched ($C_1$–$C_6$)alkyl, linear or branched ($C_1$–$C_6$)alkoxy, hydroxy, linear or branched ($C_1$–$C_6$) trihaloalkyl, amino (optionally substituted by one or more linear or branched ($C_1$–$C_6$)alkyl groups), aryl and diarylmethyl. Of the heterocycloalkyl groups, the following groups may be mentioned without implying any limitation: azetidinyl, pyrrolidinyl, piperidyl, dihydrocyclopenta[b]pyridyl.

Preferred compounds of formula (I) are those in which n is 1.

The ring

as defined for formula (I) is preferably a pyrrolidinyl group. When

represents a pyrrolidine ring, the ring is preferably in the S configuration.

Preferred $R_1$ groups are linear or branched ($C_1$–$C_6$)alkyl groups substituted by one or more aryl or heteroaryl groups.

More especially, preferred $R_1$ groups are linear or branched ($C_1$–$C_6$)alkyl groups substituted by one or more phenyl or pyridyl groups.

Preferably, the $R_1$ groups are (2,2-diphenyl)ethyl or (2-pyridyl)ethyl groups.

When $R_2$ represents a group b, X preferably represents a CH group and $R_5$ preferably represents a group HN=C (NHOH)— or Rc—$(CH_2)_m$—Y. In that case, $R_c$ will be more especially a pyridine, pyrrolidinone, imidazole or imidazoline group.

When $R_2$ represents a bicyclic system c, that system will preferably be either one in which X represents a CH group, in which case B will represent a morpholinone, isoxazole or pyrrole ring, or one in which X represents a nitrogen atom, in which case B will represent a phenyl ring.

The following are preferred compounds of the invention:
 (6S)-N-{4-[amino(hydroxyimino)methyl]benzyl}-3-[(2,2-diphenylethyl)amino]-4-oxo-4,6,7,8-tetrahydropyrrolo[1,2-a]pyrazine-6-carboxamide,
 (6S)-N-{4-[amino(hydroxyimino)methyl]benzyl}-4-oxo-3-{(2-(2-pyridyl)ethyl]-amino}-4,6,7,8-tetrahydropyrrolo[1,2-a]pyrazine-6-carboxamide,
 (6S)-N-[2-({[amino(imino)methyl]amino}oxy)ethyl]-3-[(2,2-diphenylethyl)amino]-4-oxo-4,6,7,8-tetrahydropyrrolo[1,2-a]pyrazine-6-carboxamide,
 (6S)-4-oxo-N-[(3-oxo-3,4-dihydro-2H-benzoxazin-8-yl)methyl]-3-{[2-(2-pyridyl)-ethyl]amino}-4,6,7,8-tetrahydropyrrolo[1,2-a]pyrazine-6-carboxamide,
 (6S)-4-oxo-3-{[2-(2-pyridyl)ethyl]amino}-N-[2-(2-pyridylmethoxy)benzyl]-4,6,7,8-tetrahydropyrrolo[1,2-a]pyrazine-6-carboxamide,
 (6S)-4-oxo-N-{2-[(2-oxo-3-pyrrolidinyl)oxy]benzyl}-3-{[2-(2-pyridyl)ethyl]amino}-4,6,7,8-tetrahydropyrrolo[1,2-a]pyrazine-6-carboxamide,
 (6S)-N-[2-(4,5-dihydro-1H-imidazol-2-ylmethoxy)benzyl]-4-oxo-3-{[2-(2-pyridyl)-ethyl]amino}-4,6,7,8-tetrahydropyrrolo[1,2-a]pyrazine-6-carboxamide, (6S)-N-[2-(1H-imidazol-2-ylmethoxy)benzyl]-4-oxo-3-{[2-(2-pyridyl)ethyl]amino}-4,6,7,8-tetrahydropyrrolo[1,2-a]pyrazine-6-carboxamide, (6S)-N-[1H-indol-6-ylmethyl)-4-oxo-3-{[2-(2-pyridyl)ethyl]amino}-4,6,7,8-tetrahydropyrrolo[1,2-a]pyrazine-6-carboxamide, The invention relates also to a process for the preparation of the compounds of formula (I) which is characterised in that a compound of formula (II):

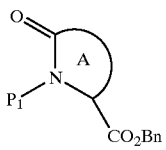
(II)

wherein A is as defined for formula (I), $P_1$ represents an amino function-protecting group and Bn represents a benzyl group, is reduced using an appropriate reducing agent to yield a compound of formula (III):

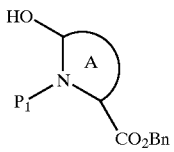
(III)

wherein A, $P_1$ and Bn are as defined hereinbefore, the hydroxy function of which compound of formula (III) is converted into methoxy and then into a cyano function by conventional reactions of organic chemistry to yield, after deprotection of the amino function, a compound of formula (IV):

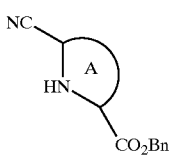
(IV)

wherein A and Bn are as defined hereinbefore,
which compound of formula (IV) is reacted with oxalyl chloride to yield a compound of formula (V):

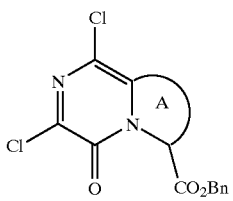
(V)

wherein A and Bn are as defined hereinbefore,
which compound of formula (V) is reacted with a compound of formula (VI):

(VI)

wherein $R_1$ is as defined for formula (I), to yield a compound of formula (VII):

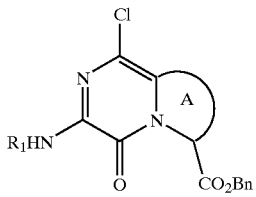
(VII)

wherein A, Bn and $R_1$ are as defined hereinbefore,
which compound of formula (VII) is then converted by catalytic hydrogenation into a compound of formula (VIII):

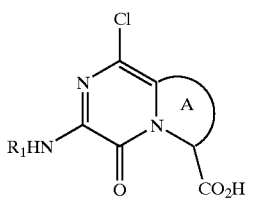
(VIII)

wherein A and $R_1$ are as defined hereinbefore,
which compound of formula (VIII) is then converted, by catalytic hydrogenation in alkaline medium, into a compound of formula (IX):

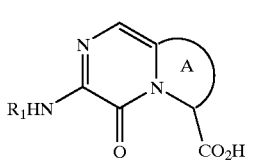
(IX)

wherein A and $R_1$ are as defined hereinbefore,
which compound of formula (IX) is reacted with a compound of formula (X):

(X)

wherein n and $R_2$ are as defined for formula (I),
to yield, after possible deprotection, a compound of formula (I),
which compound of formula (I) is optionally converted into the corresponding N-oxide, is purified, if desired, according to a conventional purification technique, is separated, if desired, into its isomers according to a conventional separation technique, and is converted, if desired, into addition salts with a pharmaceutically acceptable acid or base.

The compounds of formula (II) are obtained by benzylation of the corresponding acids.

In addition to the fact that the compounds of the present invention are new, they have especially valuable pharmacological properties.

They are potent inhibitors of trypsin-related serine proteases, exhibiting a significant selectivity in respect of thrombin compared with other coagulation and fibrinolysis serine proteases.

Those properties thus render them useful in the treatment of stable or unstable angina, disorders of thrombotic origin and/or giving rise to thrombotic complications, in the treatment or prevention of myocardial infarction and venous or arterial thromboses, and also in the treatment of the complications of vascular and cardiovascular diseases, such as atherosclerosis, arteritis, venous disease, and in the treatment of all disorders in which the formation and/or activity of thrombin is involved.

They may equally be used in therapeutic association with a thrombolytic.

The invention extends also to pharmaceutical compositions comprising as active ingredient a compound of formula (I) together with one or more suitable inert, non-toxic excipients. Among the pharmaceutical compositions according to the invention there may be mentioned more especially those which are suitable for oral, parenteral (intravenous or subcutaneous) or nasal administration, tablets or dragees, sublingual tablets, gelatin capsules, lozenges, suppositories, creams, ointments, dermal gels, injectable preparations, drinkable suspensions etc.

The useful dosage can be adapted in accordance with the nature and the severity of the disorder, the administration route and also the age and weight of the patient. That dosage varies from 1 to 500 mg per day taken in one or more administrations.

The following Examples illustrate the invention but do not limit it in any way.

The starting materials used are known products or are prepared according to known procedures.

The structures of the compounds described in the Examples were determined according to customary spectrophotometric techniques (infrared, NMR, mass spectrometry, . . . ).

EXAMPLE 1

(6S)-N-{4-[amino(hydroxyimino)methyl]benzyl}-3-[(2,2-diphenyl-ethyl)amino]-4-oxo4,6,7,8-tetrahydropyrrolo[1,2-a]pyrazine-6-carboxamide To 2.5 mmol of (6S)-3-[(2,2-diphenylethyl)amino]-4-oxo-4,6,7,8-tetrahydropyrrolo[1,2-a]pyrazine-6-carboxylic acid obtained in accordance with the process described in the Application FR 99 07538 in 50 ml of anhydrous dimethylformamide there are added 0.9 g of 4-(aminomethyl)-N'-hydroxybenzenecarboximidamide hydrochloride obtained in accordance with the process described in Synth. Comm. (28(23), 4419–4429, 1998), 1.3 ml of diisopropylethylamine and 0.4 g of hydroxybenzotriazole. After dissolution, 0.9 g of O-benzotriazolyl-tetramethylisouronium tetrafluoroborate are added and the whole is stirred for one night. After filtration and evaporation, the residue is taken up in ethyl acetate. The organic phase is washed, dried, filtered and evaporated. The expected product is obtained in solid form after purification of the residue by chromatography on silica gel using as eluant a 95/5 dichloromethane/methanol mixture.

Mass spectrum: [MH]+ m/z=522

EXAMPLE 2

(6S)-N-{4-[amino(hydroxyimino)methyl]benzyl}-4-oxo-3-{(2-(2-pyridyl)ethyl]amino}-4,6,7,8-tetrahydropyrrolo[1,2-a]pyrazine-6-carboxamide The expected product is obtained in accordance with the procedure described in Example 1, with the replacement of (6S)-3-[(2,2-diphenylethyl)amino]-4-oxo-4,6,7,8-tetrahydropyrrolo[1,2-a]pyrazine-6-carboxylic acid with (6S)-3-{[2-(2-pyridyl)ethyl]amino}-4-oxo-4,6,7,8-tetrahydropyrrolo[1,2-a]pyrazine-6-carboxylic acid.

Elemental microanalysis:

|  | C % | H % | N % |
|---|---|---|---|
| Calculated | 61.73 | 5.63 | 21.91 |
| Found | 62.03 | 5.50 | 21.78 |

EXAMPLE 3

(6S)-N-[2-({[amino(imino)methyl]amino}oxy)ethyl]-3-[(2,2-diphenyl-ethyl)amino]-4-oxo4,6,7,8-tetrahydropyrrolo[1,2-a]pyrazine-6-carboxamide dihydrochloride Step A: (6S)-N-[2-({[(tert-butyloxycarbonylamino)(tert-butyloxycarbonylimino)methyl]amino}oxy)ethyl]-3-[(2,2-diphenylethyl)amino]-4-oxo-4,6,7,8-tetrahydropyrrolo[1,2-a]pyrazine-6-carboxamide The expected product is obtained in accordance with the procedure described in Example 1, with the replacement of 4-(aminomethyl)-N'-hydroxybenzenecarboximidamide hydrochloride with N-(2-aminoethoxy)-N',N''-(di-tert-butyloxycarbonyl)guanidine.

Step B: (6S)-N-[2-({[amino(imino)methyl]amino}oxy)ethyl]-3-[(2,2-diphenylethyl)-amino]-4-oxo-4,6,7,8-tetrahydropyrrolo[1,2-a]pyrazine-6-carboxamide dihydrochloride 10 ml of a 4M solution of hydrochloric acid in dioxane are added to 1.8 mmol of the compound described in the above Step in 20 ml of anhydrous dichloromethane. The whole is stirred for one night at ambient temperature. After evaporation of the solvents, the residue is taken up in water. The solution is filtered and lyophilised and yields the expected product.

Mass spectrum: [M+H+] m/z=475

The Examples which follow were prepared in accordance with the procedure described in Example 1, using the corresponding starting materials.

EXAMPLE 4

(6S)-4-oxo-N-[(2-oxo2,3-dihydro-1H-pyrrolo[2,3-c]pyrid-5-yl)-methyl]-3-{[2-(2-pyridyl)ethyl]amino}4,6,7,8-tetrahydropyrrolo[1,2-a]pyrazine-6-carboxamide

EXAMPLE 5

(6S)-4-oxo-N-[(2-oxo2,3-dihydro-1H-imidazo[4,5-c]pyrid-6-yl)-methyl]-3-{[2-(2-pyridyl)ethyl]amino}4,6,7,8-tetrahydropyrrolo[1,2-a]pyrazine-6-carboxamide

EXAMPLE 6

(6S)-4-oxo-N-[(2-oxo2,3-dihydro-1H-benzimidazol-4-yl)methyl]-3-{[2-(2-pyridyl)ethyl]amino}4,6,7,8-tetrahydropyrrolo[1,2-a]-pyrazine-6-carboxamide

EXAMPLE 7

(6S)-4-oxo-N-[(2-oxo-2,3-dihydro-1H-benzimidazol-5-yl)methyl]-3-{[2-(2-pyridyl)ethyl]amino}-4,6,7,8-tetrahydropyrrolo[1,2-a]-pyrazine-6-carboxamide

EXAMPLE 8

(6S)4-oxo-N-[(3-oxo-3,4-dihydro-2H-benzoxazin-8-yl)methyl]-3-{[2-(2-pyridyl)ethyl]amino}-4,6,7,8-tetrahydropyrrolo[1,2-a]pyrazine-6-carboxamide

EXAMPLE 9

(6S)-4-oxo-N-[(4-oxo-3,4-dihydro-2H-1,3-benzoxazin-8-yl)methyl]-3-{[2-(2-pyridyl)ethyl]amino}-4,6,7,8-tetrahydropyrrolo[1,2-a]-pyrazine-6-carboxamide

EXAMPLE 10

(6S)-4-oxo-3-{[2-(2-pyridyl)ethyl]amino}-N-[2-(2-pyridylmethoxy)-benzyl]-4,6,7,8-tetrahydropyrrolo[1,2-a]pyrazine-6-carboxamide

EXAMPLE 11

(6S)-N-{2-[(2,4-dioxo-1,3-thiazolidin-5-yl)methyl]benzyl}-4-oxo-3-{[2-(2-pyridyl)ethyl]amino}-4,6,7,8-tetrahydropyrrolo[1,2-a]pyrazine-6-carboxamide

EXAMPLE 12

(6S)-N-{2-[(2,4-dioxo-1,3-thiazolidin-5-yl)oxy]benzyl}-4-oxo-3-{[2-(2-pyridyl)ethyl]amino}-4,6,7,8-tetrahydropyrrolo[1,2-a ]pyrazine-6-carboxamide

EXAMPLE 13

(6S)-4-oxo-N-{2-[(5-oxo4,5-dihydro-3H-1,2,4-triazol-3-yl)oxy]benzyl}-3-{[2-(2-pyridyl)ethyl]amino}-4,6,7,8-tetrahydropyrrolo[1,2-a]pyrazine-6-carboxamide

EXAMPLE 14

(6S)-4-oxo-N-{2-[(2-oxo-3-pyrrolidinyl)oxy]benzyl}-3-{[2-(2-pyridyl)ethyl]amino}-4,6,7,8-tetrahydropyrrolo[1,2-a]pyrazine-6-carboxamide

EXAMPLE 15

(6S)-N-[2-(4,5-dihydro-1H-imidazol-2-ylmethoxy)benzyl]4-oxo-3-{[2-(2-pyridyl)ethyl]amino}-4,6,7,8-tetrahydropyrrolo[1,2-a]-pyrazine-6-carboxamide

EXAMPLE 16

(6S)-N-[2-(1H-imidazol-2-ylmethoxy)benzyl]-4-oxo-3-{[2-(2-pyridyl)ethyl]amino}-4,6,7,8-tetrahydropyrrolo[1,2-a]pyrazine-6-carboxamide

EXAMPLE 17

(6S)-N-[3-amino-1,2-benzisoxazol-6-yl)methyl]-4-oxo-3-{[2-(2-pyridyl)ethyl]amino}-4,6,7,8-tetrahydropyrrolo[1,2-a]pyrazine-6-carboxamide

EXAMPLE 18

(6S)-N-[1H-indol-6-ylmethyl)-4-oxo-3-{[2-(2-pyridyl)ethyl]amino}-4,6,7,8-tetrahydropyrrolo[1,2-a]pyrazine-6-carboxamide

EXAMPLE 19

(6S)-N-[3-isoquinolinylmethyl)-4-oxo-3-{[2-(2-pyridyl)ethyl]amino}-4,6,7,8-tetrahydropyrrolo[1,2-a]pyrazine-6-carboxamide

EPHARMACOLOGICAL STUDY OF THE COMPOUNDS OF THE INVENTION

EXAMPLE A

Inhibition of Thrombin and of Fibrinolysis Serine Proteases

For in vitro evaluation of the inhibitory activity of the products of the invention on human thrombin (Sigma, specific activity 3230 NIH units/mg), purified human fibrinogen (4 mM, Stago) (Fg) was added to a given amount of thrombin (0.7 nM) that had previously been incubated with or without the inhibitor to be tested (20° C., 10 minutes).

For in vitro evaluation of the selectivity of the products in respect of plasmin, the same protocol was applied to purified human plasmin (2 nM, Stago), using as substrate a paranitroanilide-containing peptide: <Glu-Phe-Lys-pNA (0.50 mM, S 2403, Kabi).

Inhibitors, enzymes and substrates are diluted in the same buffer (0.01 mM phosphate buffer, pH 7.4, containing 0.12M sodium chloride and 0.05% bovine serum albumin) and then distributed in a polystyrene microtitre plate in a volume of 50 μl.

The fibrin formed by the thrombin or by the paranitroanilide released by the action of the serine protease is measured spectrophotometrically at 405 nm after from 15 to 30 minutes' reaction at 20° C.

In this test it was demonstrated in particular that the concentration in nM inhibiting the enzymatic activity of thrombin by 50% ($IC_{50}$) compared with the control without product is 141 nM for the compound of Example 1, 310 nM for the compound of Example 2, 4 nM for the compound of Example 3, 136 nM for the compound of Example 10, 12 nM for the compound of Example 15, 140 nM for the compound of Example 17 and 22 nM for the compound of Example 18.

the compounds of the invention are furthermore very selective in respect of thrombin compared with other fibrinolytic serine proteases (plasmin, tPa and uPa).

EXAMPLE B

Anti-coagulant Activity, Measurement of Thrombin Time and Activated Cephalin Time in Man.

In order to evaluate the anti-coagulant activity of the compounds of the invention, the thrombin time (TT) and the activated cephalin time (ACT) were determined in human plasma samples. An $ST_4$ coagulometer was used. A plasma deficient in platelets is lyophilised and taken up in distilled water. The TT is obtained using the reagent Thrombine Prest and the ACT is obtained using the reagent Céphaline PTT Automate. Inhibitor or solvent (10 μl) is added to the plasma (90 μl), which is then incubated for 2 minutes at 37° C. 100 μl of Thrombine Prest (TT) or of Céphaline PTT Automate (ACT) are added and at the same time the timer is started.

Under those conditions, the TT is of the order of 18 seconds and the ACT of the order of 12 seconds. The activity of an antagonist is evaluated by its capacity to prolong the TT and the ACT relative to the control. The effect of the inhibitors is expressed by the concentration in μM that doubles the coagulation time ($Ctt_2$).

The compounds of the invention caused very significant prolongation of the coagulation times and a number of the $Ctt_2$ are illustrated by way of example in Table 1 hereinbelow:

TABLE 1

| Example | TT Ctt$_2$ ($\mu$M) | ACT Ctt$_2$ ($\mu$M) |
| --- | --- | --- |
| 2 | 3.6 | 20 |
| 3 | 0.10 | 1.1 |
| 15 | 0.19 | 1.91 |
| 18 | 0.28 | 3.07 |

PHARMACEUTICAL COMPOSITION EXAMPLE

Formulation for the preparation of 1000 tablets each comprising 10 mg of active ingredient:

| | |
| --- | --- |
| compound of Example 1 | 10 g |
| hydroxypropyl cellulose | 2 g |
| wheat starch | 10 g |
| lactose | 100 g |
| magnesium stearate | 3 g |
| talc | 3 g |

What is claimed is:

1. A compound of formula (I):

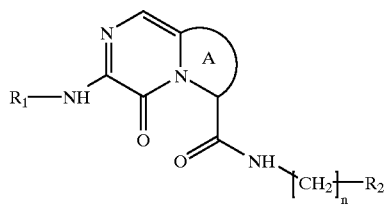

(I)

wherein $R_1$ represents hydrogen, or linear or branched ($C_1$–$C_6$) alkyl optionally substituted by one or more identical or different groups selected from aryl, heteroaryl, cycloalkyl and heterocycloalkyl,

represents a saturated ring having from 4 to 7 ring members that may contain, in addition to nitrogen, one or two hetero atoms selected from O, S and —$NR_3$, wherein $R_3$ represents hydrogen or linear or branched ($C_1$–$C_6$)alkyl, n represents an integer such that $1 \leq n \leq 6$, $R_2$ is selected from of the following groups:

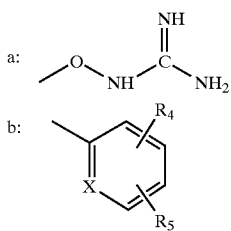

wherein:
  X represents CH or nitrogen,
  $R_4$ represents hydrogen or halogen,
  $R_5$ represents any one of the groups:
    $R_a$NHCOHN— wherein $R_a$ represents hydrogen or linear or branched ($C_1$–$C_6$)alkyl,
    $R_b$SO$_2$NHCO(NH)$_p$—, wherein $R_b$ represents linear or branched ($C_1$–$C_6$)alkyl and p represents 0 or 1,
    HON=C(NH$_2$)—, HN=C(NHOH)—,
    $R_c$—(CH$_2$)$_m$—Y— wherein:
      Y represents CH$_2$, O, S or $R_a$N, m represents a integer such that $0 \leq m \leq 3$, $R_c$ represents a saturated or unsaturated heterocycle having 5 or 7 ring members containing from 1 to 4 hetero atoms selected from oxygen, nitrogen and sulphur, the heterocycle optionally containing one or more carbonyl functions and optionally being substituted by one or more identical or different substituents selected from halogen atoms, linear or branched ($C_1$–$C_6$) alkyl groups, linear or branched ($C_1$–$C_6$) alkoxy groups, and amino groups (optionally substituted by one or two linear or branched ($C_1$–$C_6$)alkyl groups), and
  c: a bicyclic system of formula

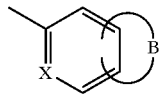

wherein:
  X is as defined hereinbefore and B, together with the carbon atoms to which it is attached, forms an aryl or a saturated or unsaturated heterocycle having 5 or 7 ring members containing from 1 to 4 hetero atoms selected from oxygen, nitrogen and sulphur, the heterocycle optionally containing at least one carbonyl function and optionally being substituted by one or more identical or different substituents selected from halogen atoms, linear or branched ($C_1$–$C_6$)alkyl groups, linear or branched ($C_1$–$C_6$)alkoxy groups, and amino groups (optionally substituted by one or two linear or branched ($C_1$–$C_6$)alkyl groups), its isomers, N-oxides and pharmaceutically acceptable addition salts thereof with an acid or a base, it being understood that aryl, phenyl, biphenyl, or naphthyl, may optionally be substituted by one or more identical or different groups selected from halogen, linear or branched ($C_1$–$C_6$)alkyl (optionally substituted by hydroxy, carboxy, amino (optionally substituted by one or two linear or branched ($C_1$–$C_6$)alkyl groups) or carbamoyl (optionally substituted by one or two linear or branched ($C_1$–$C_6$)alkyl groups)), linear or branched ($C_1$–$C_6$)alkoxy, hydroxy, linear or branched ($C_1$–$C_6$)trihaloalkyl, linear or branched ($C_1$–$C_6$) trihaloalkoxy, amino (optionally substituted by one or two linear or branched ($C_1$–$C_6$)alkyl groups), linear or branched ($C_1$–$C_6$)alkylcarbonyloxy, carboxymethoxy and carbamoylmethoxy (optionally N-substituted by one or two linear or branched ($C_1$–$C_6$)alkyl groups), heteroaryl being understood to be an aromatic mono- or bi-cyclic group having from 5 to 12 ring members containing one, two or three hetero atoms selected from oxygen, nitrogen and sulphur, wherein the heteroaryl may be optionally substituted by one or more identical or different groups selected from halogen, linear or branched ($C_1$–$C_6$)alkyl (optionally substituted by hydroxy, carboxy, amino (optionally substituted by one or two linear or branched ($C_1$–$C_6$)alkyl groups) or carbamoyl (optionally substituted by one or two linear or branched ($C_1$–$C_6$)alkyl groups)), hydroxy, linear or branched ($C_1$–$C_6$)alkoxy, linear or branched (C$_1$–C$_6$)trihaloalkyl, phenyl, amino (optionally N-substituted by one or more linear or branched (C$_1$–C$_6$) alkyl groups), carboxymethoxy and carbamoylmethoxy (optionally substituted by one or two linear or branched (C$_1$–C$_6$)alkyl groups), cycloalkyl being understood to be a saturated or unsaturated, mono- or bi-cyclic hydrocarbon group having from 3 to 12 ring members, wherein the ring may optionally be substituted by one or more identical or different groups selected from halogen, linear or branched (C$_1$–C$_6$)alkyl, linear or branched (C$_1$–C$_6$)alkoxy, hydroxy, linear or branched (C$_1$–C$_6$)trihaloalkyl, amino (optionally substituted by one or more linear or branched (C$_1$–C$_6$)alkyl groups) and aryl, a heterocycloalkyl group being understood to be a saturated or unsaturated, mono- or bi-cyclic group having from 4 to 12 ring members containing one, two or three hetero atoms selected from oxygen, nitrogen and sulphur, wherein the heterocycle may optionally be substituted by one or more identical or different groups selected from halogen, linear or branched (C$_1$–C$_6$)alkyl, linear or branched (C$_1$–C$_6$)alkoxy, hydroxy, linear or branched (C$_1$–C$_6$)trihaloalkyl, amino (optionally substituted by one or more linear or branched (C$_1$–C$_6$)alkyl groups), aryl and diarylmethyl.

2. A compound of claim 1, wherein n is 1.

3. A compound of claim 1 wherein ring

is pyrrolidinyl.

4. A compound of claim 1, wherein R$_1$ represents linear or branched (C$_1$–C$_6$)alkyl substituted by one or more aryl or heteroaryl groups.

5. A compound of claim 4, wherein aryl is phenyl.

6. A compound of claim 4, wherein heteroaryl is pyridyl.

7. A compound of claim 1, wherein R$_2$ represents

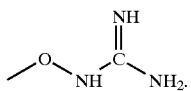

8. A compound of claim 1, wherein R$_2$ represents

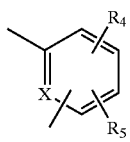

wherein
X represents CH or nitrogen,
R$_4$ represents hydrogen or halogen,
R$_5$ represents any one of the groups:
R$_a$NHCOHN— wherein R$_a$ represents hydrogen or linear or branched (C$_1$–C$_6$)alkyl,
R$_b$SO$_2$NHCO(NH)$_p$—, wherein R$_b$ represents linear or branched (C$_1$–C$_6$)alkyl and p represents 0 or 1,
HON=C(NH$_2$)—, HN=C(NHOH)—,
R$_c$—(CH$_2$)$_m$—Y— wherein:
Y represents CH$_2$, O, S or R$_a$N, m represents an integer such that 0≦m≦3, R$_c$ represents a saturated or unsaturated heterocycle having 5 or 7 ring members containing from 1 to 4 hetero atoms selected from oxygen, nitrogen and sulphur, the heterocycle optionally containing one or more carbonyl functions and optionally being substituted by one or more identical or different substituents selected from halogen atoms, linear or branched (C$_1$–C$_6$)alkyl groups, linear or branched (C$_1$–C$_6$)alkoxy groups, and amino groups (optionally substituted by one or two linear or branched (C$_1$–C$_6$)alkyl groups).

9. A compound of claim 1, wherein R$_2$ represents a bicyclic system of formula

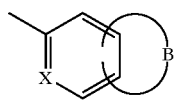

wherein X represents CH or nitrogen, and B together with the carbon atoms to which it is attached, forms a saturated or unsaturated heterocycle having 5 or 7 ring members containing from 1 to 4 hetero atoms selected from oxygen, nitrogen and sulphur, the heterocycle optionally containing at least one carbonyl function and optionally being substituted by one or more identical or different substituents selected from halogen atoms, linear or branched (C$_1$–C$_6$) alkyl groups, linear or branched (C$_1$–C$_6$)alkoxy groups, and amino groups (optionally substituted by one or two linear or branched (C$_1$–C$_6$)alkyl groups).

10. The compound of claim 1, which is (6S)-N-{4-[amino (hydroxyimino)methyl]benzyl}-3-[(2,2-diphenylethyl) amino]-4-oxo-4,6,7,8-tetra-hydropyrrolo[1,2-a]pyrazine-6-carboxamide, its isomers, its N-oxides and pharmaceutically acceptable addition salts thereof with an acid or a base.

11. The compound of claim 1, which is (6S)-N-{4-[amino (hydroxyimino)methyl]benzyl }-4-oxo-3-{(2-(2-pyridyl) ethyl]amino }-4,6,7,8-tetrahydropyrrolo[1,2-a]pyrazine-6-carboxamide, its isomers, its N-oxides and pharmaceutically acceptable addition salts thereof with an acid or a base.

12. The compound of claim 1, which is (6S)-N-[2-({[amino(imino)methyl]amino}oxy)ethyl]-3-[(2,2-diphenylethyl)amino]-4-oxo-4,6,7,8-tetrahydropyrrolo[1,2-a]pyrazine-6-carboxamide, its isomers, its N-oxides and pharmaceutically acceptable addition salts thereof with an acid or a base.

13. The compound of claim 1, which is (6S)-4-oxo-N-[(3-oxo-3,4-dihydro-2H-benzoxazin-8-yl)methyl]-3-{[2-(2-pyridyl)ethyl]amino}-4,6,7,8-tetrahydropyrrolo[1,2-a] pyrazine-6-carboxamide, its isomers, its N-oxides and pharmaceutically acceptable addition salts thereof with an acid or a base.

14. The compound of claim 1, which is (6S)-4-oxo-3-{[2-(2-pyridyl)ethyl]amino}-N-[2-(2-pyridylmethoxy) benzyl]-4,6,7,8-tetrahydropyrrolo[1,2-a]pyrazine-6-carboxamide, its isomers, its N-oxides and pharmaceutically acceptable addition salts thereof with an acid or a base.

15. The compound of claim 1, which is (6S)-4-oxo-N-{2-[(2-oxo-3-pyrrolidinyl)oxy]benzyl}-3-{[2-(2-pyridyl) ethyl]amino}-4,6,7,8-tetrahydropyrrolo[1,2-a]pyrazine-6-carboxamide, its isomers, its N-oxides and pharmaceutically acceptable addition salts thereof with an acid or a base.

16. The compound of claim 1, which is (6S)-N-[2-(4,5-dihydro-1H-imidazol-2-ylmethoxy)benzyl]-4-oxo-3-{[2-(2-pyridyl)ethyl]amino}-4,6,7, 8-tetrahydro-pyrrolo[1,2-a] pyrazine-6-carboxamide, its isomers, its N-oxides and pharmaceutically acceptable addition salts thereof with an acid or a base.

17. The compound of claim 1, which is (6S)-N-[2-(1H-imidazol-2-ylmethoxy)benzyl]-4-oxo-3-{[2-(2-pyridyl)

ethyl]amino}-4,6,7,8-tetrahydropyrrolo[1,2-a]pyrazine-6-carboxamide, its isomers, its N-oxides and pharmaceutically acceptable addition salts thereof with an acid or a base.

18. The compound of claim 1, which is (6S)-N-[1H-indol-6-yl-methyl)-4-oxo-3-{[2-(2-pyridyl)ethyl]amino}-4,6,7,8-tetrahydropyrrolo[1,2-a]pyrazine-6-carboxamide, its isomers, its N-oxides and pharmaceutically acceptable addition salts thereof with an acid or a base.

19. A method for treating an animal or human living body afflicted with a condition requiring an inhibitor of trypsin-related serine proteases comprising the step of administering to the living body a therapeutically effective amount of a compound of claim 1, which is effective for alleviation of said condition.

20. A pharmaceutical composition useful in treating an animal or human living body afflicted with a condition requiring an inhibitor of trypsin-related serine proteases comprising as active principle a therapeutically effective amount of a compound as claimed in claim 1, together with one or more pharmaceutical acceptable excipients or vehicles.

21. A method for treating an animal or human living body afflicted with a condition requiring a thrombin inhibitor comprising the step of administering to the living body a therapeutically effective amount of a compound of claim 1, which is effective for alleviation of said condition.

22. A pharmaceutical composition useful in treating an animal or human living body afflicted with a condition requiring a thrombin inhibitor comprising as active principle a therapeutically effective amount of a compound as claimed in claim 1, together with one or more pharmaceutical acceptable excipients or vehicles.

* * * * *